US006952653B2

(12) United States Patent
Toth et al.

(10) Patent No.: US 6,952,653 B2
(45) Date of Patent: Oct. 4, 2005

(54) SINGLE TOOL DEFECT CLASSIFICATION SOLUTION

(75) Inventors: Gabor D. Toth, San Jose, CA (US); David R. Bakker, Cupertino, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/705,059

(22) Filed: Nov. 10, 2003

(65) Prior Publication Data

US 2005/0033528 A1 Feb. 10, 2005

Related U.S. Application Data

(60) Provisional application No. 60/466,816, filed on Apr. 29, 2003.

(51) Int. Cl.⁷ ............................. G01B 5/28; G06K 9/00
(52) U.S. Cl. ........................................ 702/35; 382/149
(58) Field of Search .............................. 702/35, 83, 84; 382/149, 145; 700/110

(56) References Cited

U.S. PATENT DOCUMENTS

| | | | |
|---|---|---|---|
| 5,699,447 A | 12/1997 | Alumot et al. ............... | 382/145 |
| 5,991,699 A | 11/1999 | Kulkarni et al. .............. | 702/83 |
| 6,104,835 A | 8/2000 | Han ........................... | 382/225 |
| 6,169,282 B1 | 1/2001 | Maeda et al. ................ | 250/310 |
| 6,208,751 B1 | 3/2001 | Almogy ...................... | 382/149 |
| 6,259,520 B1 | 7/2001 | Zeimantz .................. | 356/237.4 |
| 6,300,629 B1 | 10/2001 | Lawrence .................... | 250/310 |
| 6,324,298 B1 | 11/2001 | O'Dell et al. ................ | 382/149 |
| 6,407,386 B1 | 6/2002 | Dotan et al. ................. | 250/310 |
| 6,408,219 B2 | 6/2002 | Lamey et al. ................ | 700/110 |
| 6,424,881 B1 | 7/2002 | Steffan et al. .............. | 700/121 |
| 6,426,501 B1 | 7/2002 | Nakagawa ................... | 250/310 |
| 6,438,438 B1 | 8/2002 | Takagi et al. ................ | 700/121 |
| 6,521,466 B1 | 2/2003 | Castrucci ........................ | 438/5 |
| 6,542,830 B1 | 4/2003 | Mizuno et al. ............... | 702/35 |
| 6,583,414 B2 | 6/2003 | Nozoe et al. ................ | 250/310 |
| 6,610,980 B2 | 8/2003 | Veneklasen et al. ......... | 250/310 |
| 6,635,872 B2 | 10/2003 | Davidson ..................... | 250/307 |
| 6,674,890 B2 | 1/2004 | Maeda et al. ................ | 382/149 |
| 6,701,259 B2 | 3/2004 | Dor et al. ...................... | 702/35 |
| 6,744,266 B2 | 6/2004 | Dor et al. .................... | 324/751 |
| 6,757,621 B2 | 6/2004 | Mizuno et al. ............... | 702/35 |
| 2004/0038454 A1 | 2/2004 | Coldren et al. ............. | 438/122 |

OTHER PUBLICATIONS

Yoda et al., An Automatic Wafer Inspection System Using Pipelined Image Processing, Jan. 1988, IEEE Transactions on Pattern Analysis and Machine Intelligence, vol. 10, No. 1.

Ben–Porath et al., Advanced Process Development and Control Based on a Fully Automated SEM with ADC, 1999, IEEE/SEMI Advanced Semiconductor Manufacturing Conference.

Rehani et al., An Automated Recipe–Based Defect Analysis System for ASICs, SEMICON 1999, Yield Management Solutions, pp. 40–43.

Fan et al., Effective defect detection and Classification Methodology Based on Integrated Laser Scanning Inspection and Automatic Defect Classification, 1998, IEEE/SEMI Advanced Semiconductor Manufacturing Conference.

*Primary Examiner*—Michael Nghiem
*Assistant Examiner*—Toan M. Le
(74) *Attorney, Agent, or Firm*—Beyer, Weaver & Thomas, LLP.

(57) ABSTRACT

Methods and apparatus for efficiently analyzing defects in-line on a wafer by wafer basis are provided. In general terms, embodiments of the present invention provide a simple interface for setting up the entire inspection and defect analysis process in a single set up procedure. The apparatus includes an inspection station for inspecting a specimen for potential defects and a review station for analyzing a sample of the potential defects to determine a classification of such potential defects. The apparatus further includes a computer system having an application interface operable to allow a user to set up the inspection station and the review station during a same setup phase so as to allow the inspection station and the review station to then operate automatically to provide defect information for one or more specimens based on the user set up.

23 Claims, 7 Drawing Sheets

SINGLE TOOL DEFECT CLASSIFICATION SOLUTION

CROSS REFERENCE TO RELATED PATENT APPLICATION

This application claims priority of U.S. Provisional Patent Application No. 60/466,816, entitled SINGLE TOOL DEFECT CLASSIFICATION SOLUTION, filed 29 Apr. 2003 by Gabor D. Toth et al., which application is incorporated herein by reference in its entirety for all purposes.

This application is related to United States Application, having application Ser. No. 10/298,389, entitled "INSPECTION SYSTEM SETUP TECHNIQUES", filed 14 Nov. 2002, by David Bruce Coldren et al. and U.S. Provisional Application, having application No. 60/445,768, entitled "WATERFALL SETUP FOR SURFACE INSPECTION TOOLS", filed 6 Feb. 2003, by Cecilia A. Campochiaro et al. These applications are incorporated herein by reference in their entirety for all purposes.

BACKGROUND OF THE INVENTION

The present invention relates generally to semiconductor inspection and defect analysis techniques, and more specifically to techniques for setting up the inspection and defect analysis apparatus.

Generally, the industry of semiconductor manufacturing involves highly complex techniques for fabricating integrating circuits using semiconductor materials. Due to the large scale of circuit integration and the decreasing size of semiconductor devices, the semiconductor manufacturing process is prone to processing defects. Testing procedures are therefore critical to maintain quality control. Since the testing procedures are an integral and significant part of the manufacturing process, the semiconductor industry is constantly seeking for more accurate and efficient testing procedures.

Typical inspection processes detect defects by comparing similar semiconductor device areas on a wafer. The differences detected between the two device areas can either be a defect, which can cause a device to function improperly, or a nuisance, which will not affect system operations. An integral phase of semiconductor wafer inspection involves optimizing the settings, commonly referred to as the "recipe," of an inspection device so that it can accurately distinguish defects from nuisances.

After potential defects are found by an inspection system, the wafer is typically transferred to a review tool for classification of the defects. However, classification of the defects requires optimizing the settings of the review tool, also referred to as a "recipe", so that the review tool can adequately classify the potential defects or determine that the potential defects are nuisances or false defects.

In sum, analysis of the defects on a particular wafer lot requires setting up and optimizing a recipe for an inspection tool and setting up a different recipe for the review tool. Setting up two recipe for two different tools is time consuming and complex. Additionally, conventional inspection and review tools typically require batch type processing of and entire cassette of wafers. That is, a cassette is first loaded into the inspection tool for localization of potential defects. After the entire cassette is inspected, the entire cassette is then loaded into the review tool for defect analysis. This batch type processing prevent the full adoption of true in-line monitoring of the manufacturing process. For example, adjustment of the defect inspection and sampling process based on information gained from defect review within a same lot is impossible in conventional testing systems.

Thus, improved apparatus and techniques for analyzing defects are needed. More specifically, techniques and apparatus for efficiently setting up recipes for such apparatus are required.

SUMMARY OF THE INVENTION

Accordingly, apparatus and techniques are provided for efficiently analyzing defects in-line on a wafer by wafer basis. In general terms, embodiments of the present invention provide a simple interface for setting up the entire inspect and defect analysis process in a single set up procedure. In one embodiment, an apparatus for analyzing defects on specimens is disclosed. The apparatus includes an inspection station for inspecting a specimen for potential defects and a review station for analyzing a sample of the potential defects to determine a classification of such potential defects. The apparatus further includes a computer system having an application interface operable to allow a user to set up the inspection station and the review station during a same setup phase so as to allow the inspection station and the review station to then operate automatically to provide defect information for one or more specimens based on the user set up.

In a specific implementation, the inspection station and the review station are integrated together into a single tool. In another implementation, the application interface is implemented on either the inspection station or the review station. In another aspect, the defect information is provided by presenting it within the application interface.

In another implementation, the application interface has input fields for entry of a plurality of imaging conditions and at least one threshold parameter for the inspection station and a plurality of imaging conditions for the review station. In a further aspect, the computer system is further operable to generate a recipe for operation of the inspection station and review station based on the plurality of imaging conditions and the at least one threshold parameter for the inspection station and the plurality of imaging conditions for the review station entered by a user. In another aspect, the computer system is further operable to automatically initiate execution of the inspection station and review station based on the generated recipe. In another aspect, the computer system is further operable to automatically optimize the recipe.

In another embodiment, the invention pertains to a method for analyzing defects on specimens. User selection of a recipe for performing an inspection of the specimens for potential defects and a defect analysis of the potential defects is received. The specimens are then automatically inspected for potential defects based on the selected recipe and without receiving subsequent user input, the potential defects are automatically analyzed based on the selected recipe and defect information is provided.

In one aspect, the defect information is in the form of defect classifications of the potential defects. In a specific implementation, the defect information is in the form of pareto charts having a plurality of bars, wherein each bar represents a particular defect type and has a height corresponding to a number of defects found with the particular defect type.

In a specific embodiment, the recipe is selected by selecting an existing recipe when an existing recipe for the specimens is available and generating a new recipe when there is no existing recipe available for the specimens. In a further aspect, generating a new recipe includes (a) providing a test specimen having known defects; (b) setting inspection imaging conditions and one or more threshold parameters for inspecting the test specimen for potential defects and setting review imaging conditions for analyzing the potential defects of the test specimen; (c) under the inspection imaging conditions, performing an inspection on the test specimen to locate potential defects based on the threshold parameters; (d) under the review imaging conditions, performing a defect analysis of the potential defects located during the inspection; (e) adjusting one or more of the inspection imaging conditions, review imaging conditions, and threshold parameters until the potential defects located during the inspection and analyzed during the defect analysis substantially match the known defects of the test specimen; and (f) generating and loading a recipe based on the inspection imaging conditions, review imaging conditions, and threshold parameters when the potential defects located during the inspection and the analyzed during the defect analysis substantially match the known defects of the test specimen.

In one aspect, the defect analysis includes classifying the potential defects into defect types or nuisances, and the potential defects substantially match the known defects when the classified defect types of the potential defects substantially match the known defects' types.

In one specific implementation, the operation of automatically inspecting the specimens for potential defects and analyzing the potential defects includes (a) loading and aligning a first one of the specimens for inspection; (b) inspecting the first specimen for potential defects and providing potential defect information; (c) sampling a portion of the potential defects of the first specimen; and (d) reviewing and classifying the sampled potential defects into a plurality of defect types and providing defect information based on such review and classification.

In one aspect, operations (a) through (d) are repeated for a next specimen immediately after inspecting the first specimen. In one aspect, the selected recipe is adjusted based on the provided defect information. In another aspect, further processing of the first and the next specimen is halted based on the provided defect information. In yet another aspect, the inspection of the next specimen is halted based on the provided defect information. In another aspect, a root cause of one or more of the defect types is eliminated or minimized based on the provided defect information.

These and other features of the present invention will be presented in more detail in the following specification of the invention and the accompanying figures which illustrate by way of example the principles of the invention.

BRIEF DESCRIPTION OF THE DRAWINGS

The present invention will be readily understood by the following detailed description in conjunction with the accompanying drawings, wherein like reference numerals designate like structural elements.

DETAILED DESCRIPTION OF THE PREFERRED EMBODIMENTS

Reference will now be made in detail to the specific embodiments of the invention. Examples of the these specific embodiments are illustrated in the accompanying drawings. While the invention will be described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Figure 1:
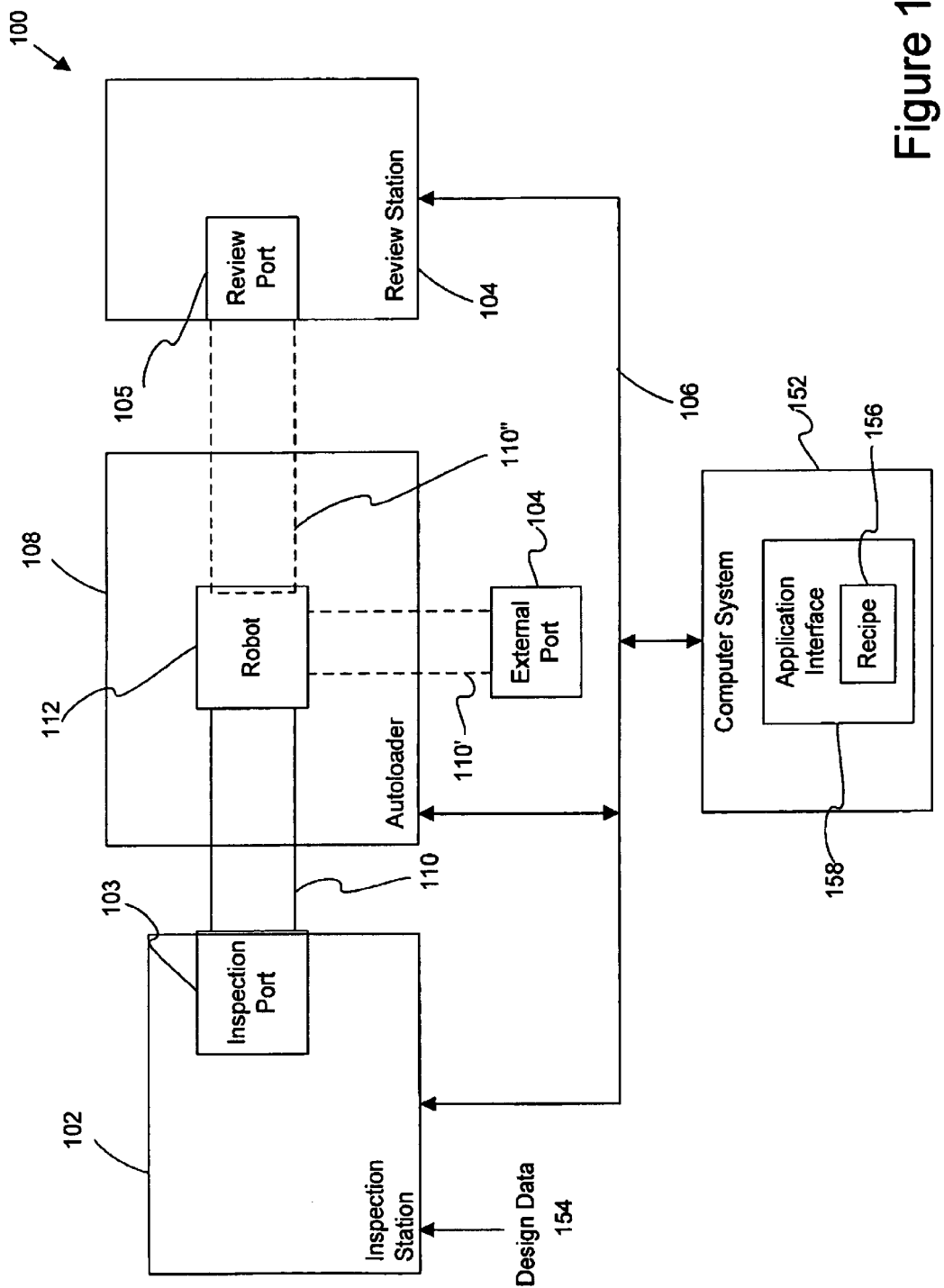
FIG. 1 is a diagrammatic representation of a Defect Analysis System for analyzing defects on a specimen in accordance with one embodiment of the present invention.

FIG. 1 is a diagrammatic representation of a Defect Analysis System 100 for analyzing defects on a specimen in accordance with one embodiment of the present invention. The specimen may be anything that requires inspection for defects, such as a semiconductor wafer or reticle. As shown, the Defect Analysis System 100 provides at least an inspection station inspection station 102 for inspecting a specimen for potential defects and a review station 104 for analyzing a sample of such potential defects. The Defect Analysis System 100 may include more than one inspection station for inspecting different types of defects, as well as more than one review station for reviewing different types of defects, for example.

The inspection station 102 and review station are coupled with a computer system 152 through which a user may set up both stations through a single application interface 158. For example, the user may set up a single recipe 156 for specifying operation of the two stations 102 and 104. In sum, the Defect Analysis System 100 advantageously includes a single application interface 152 for setting up the operating conditions of both stations 102 and 104 in a single set up phase as described further below. Alternatively, the application interface 158 for setting both the inspection and review stations may be implemented on either the inspection station 102 or the review station 104.

Although the inspection station 102 and review station 104 are shown as separate tools, a single integrated inspection and review station may be utilized. Several embodiments of such an integrated system are further described in U.S. application Ser. No. 10/638,027, filed 8 Aug. 2003, entitled "METHODOLOGIES FOR EFFICIENT INSPECTION OF TEST STRUCTURES USING ELECTRON BEAM SCANNING AND STEP AND REPEAT SYSTEMS", by Gaurav Verma et al., which application is incorporated herein by reference in its entirety for all purposes.

Once the two stations 102 and 104 are set up by a user, the two stations may then execute transparently to the user and produce defect information for one or more specimens. In sum, the single application interface 152 allows a user to set up the Defect Analysis System 100 in a single set up phase to then automatically obtain defect information regarding one or more specimens based on such user set up.

The Defect Analysis System 100 also includes a mechanism for transporting specimens between the inspection station 102 and the review station 104. In the illustrated embodiment, the Defect Analysis System 100 includes an autoloader 108 for automatically transporting specimens. The autoloader 108 includes a robot 112 having an arm which can extend to a position 110 towards an inspection port 103 of the inspection station 102. The arm may also rotate and extend to a position 110' towards an external port 104, where it is in a state denoted by reference number 110'. Similarly, when in its state denoted by reference number 110", the robotic arm can also extend towards a review station port 105 of a review station 104 for analyzing potential defects found by the inspection station 102. The robotic arm is designed to further extend and retrieve a specimen from review station 104. Alternatively, a robot having one or more arms may move between stations on a track. Any suitable automation mechanism may be utilized, and such automation mechanisms are well known to those skilled in the art.

A defect analysis process, according to one embodiment of the present invention, may begin after a plurality of specimens are placed on external port 104, with the intention of storing the specimens until one is used in a subsequent inspection application, for example. Robotic arm in its position 110' transports a specimen from external port 104 and places it in the inspection port 103 of inspection station 102. After a specimen is inspected by inspection station 102, robotic arm 110 retrieves the inspected specimen from the inspection port 103 and places it on review port 105 of review station 104 by extending the robotic arm to position 110". After a specimen is reviewed, the robotic arm may then retrieve the reviewed specimen from review port 105 and place it back into the external port 104 by moving from position 110" to position 110'.

The inspection station 102 may also include a computer system (not shown) for implementing an evaluation process in which it is determined whether the specimen has passed inspection. Alternatively, the computer system may be separate from the inspection station 102, e.g., in the form of computer system 152. In the illustrated embodiment, the inspection station 102 may receive design data 154 in the form of a list of figures, for example. Additionally, the inspection station 102 obtains image data from the specimen. The inspection station 102 then analyzes the image data by comparing it to a baseline image, which may be generated from the design data 254 or from a similar area of the specimen or a different specimen (e.g., in a die-to-die mode inspection).

After the inspection has concluded, the robot 112 moves the specimen to the review station 104. The inspection station 102 may also send a map of potential defects to the review station 104 through communication line 106. The review station 104 may also include a computer system (not shown) for implementing a defect analysis process where the potential defects are reviewed and classified. Alternatively, a computer system may be separate from the inspection station 104, e.g., in the form of computer system 152.

Suitable computer systems for use in implementing and controlling the inspection and defect analysis techniques described herein may be obtained from various vendors (e.g., Dell Computer Corporation of Round Rock, Tex.) or custom built by an inspection system vendor, such as KLA-Tencor of San Jose, Calif.

Preferably, the inspection station 102 is in the form of an optical, UV (ultra-violet), electron beam, or other inspection system that is integrated with a computer system which implements many of the inspection operations described herein. Such composite system preferably includes at least (a) a baseline image (preferably compacted) stored in memory, (b) an imaging system arranged to generate an optical or electron beam image of the specimen, and (c) a processing unit configured to compare the baseline and current test images and thereby identify defects, as well as compute and store various statistical information. At a minimum, the imaging system; will usually include (i) a source of illumination oriented to direct radiation onto a specified location of the specimen; and (ii) one or more detectors oriented to detect an image of the specimen from the source which has been scattered by the specimen. The imaging system may also include a scanning means. Suitable inspection stations include the AIT-XP, eS20XP, TeraStar, and SL3UV available from KLA-Tencor, Corp. of San Jose, Calif.

The review station 104 also preferably forms a composite system similar to the inspection station 102 to implement the review operations described herein. However, the review station 104 typically provides a higher resolution image of the specimen for analysis of defects than the images provided by the inspection station 102. Suitable reviews stations include the eV300 and CRS3100 available from KLA-Tencor, Corp. of San Jose, Calif.

In general, the inspection and review stations may take any suitable form for inspecting a sample for defects or reviewing defects. Each station may take the form of an optical system, such as a bright field or dark field optical system. The station may also utilize both bright field and dark field modes. Examples of bright field systems include the 2350, 2351, 2360, and 2370 from KLA-Tencor, Corp. of San Jose, Calif. Examples of dark field system include the AIT II, AIT XP, Fusion, Fusion UV, and SP1 PatternPro available from KLA-Tencor, Corp. of San Jose, Calif. Each stations may also take the form of an electron beam (ebeam) system, such as a scanning, snapshot, or step-and-repeat type ebeam system. A station may be designed to detect special types of defects, such as macro defects across a large area of the sample, defects on a bare substrate, or defects within solder bumps (e.g., ball grid array bumps). Each station may also be stand alone or integrated within a processing tool.

Figure 2:
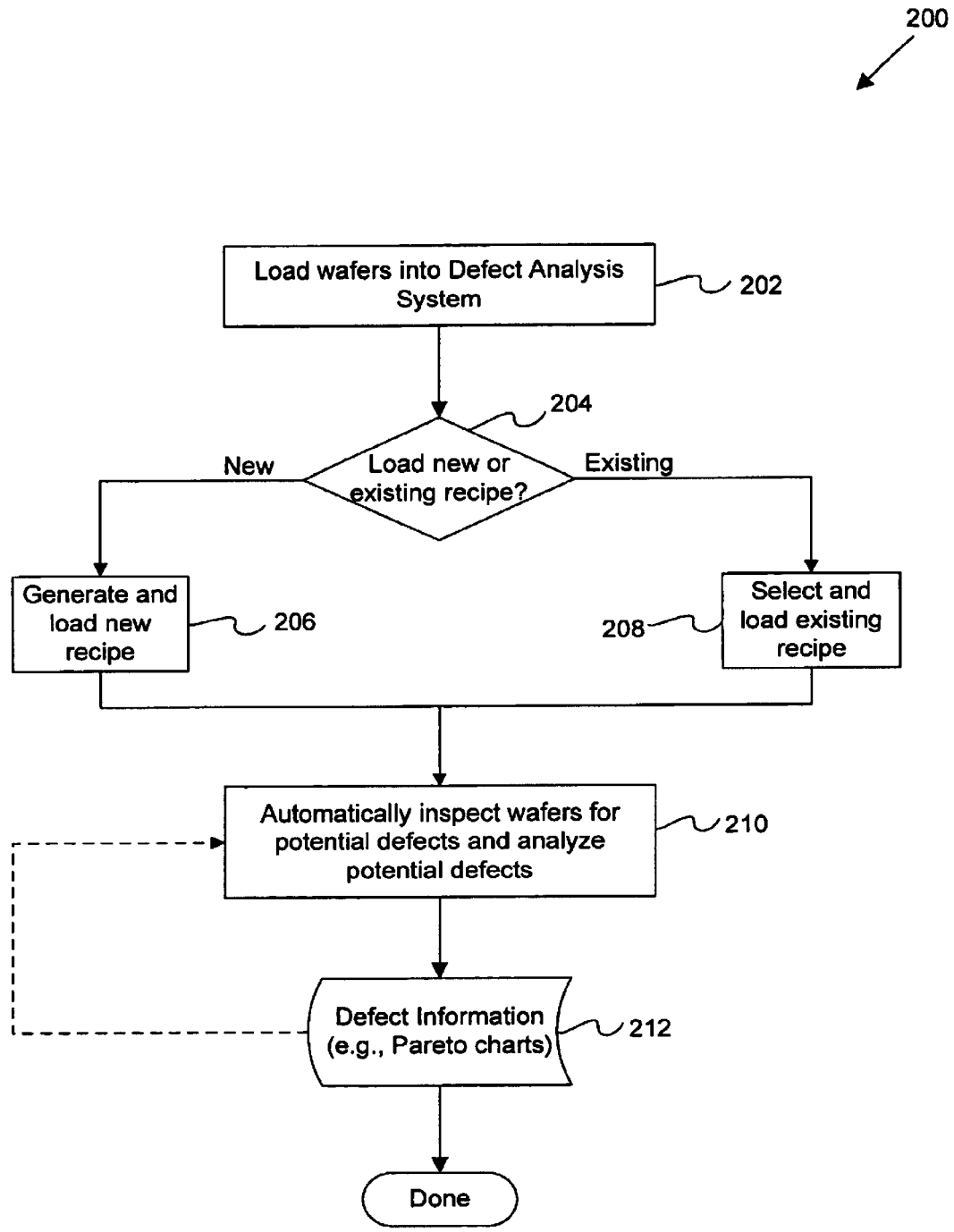
FIG. 2 is a flowchart illustrating a procedure for automatically inspecting specimens for potential defects and analyzing the potential defects in accordance with one embodiment of the present invention.

FIG. 2 is a flowchart illustrating a procedure 200 for automatically inspecting specimens for potential defects and analyzing the potential defects in accordance with one embodiment of the present invention. The Defect Analysis System 100 of FIG. 1 will be utilized to describe the operations of FIG. 2. Initially, a plurality of specimens or wafers are loaded into the Defect Analysis System 100 in operation 202. Either a new or existing recipe for the loaded specimens is then selected and loaded in operation 204. If an existing recipe for the loaded specimens is available, an existing recipe is then selected by the user and loaded in operation 208. However, if a new recipe is required for the loaded specimens, a new recipe is generated by the user for the loaded specimens and loaded in operation 206.

Figure 6A:
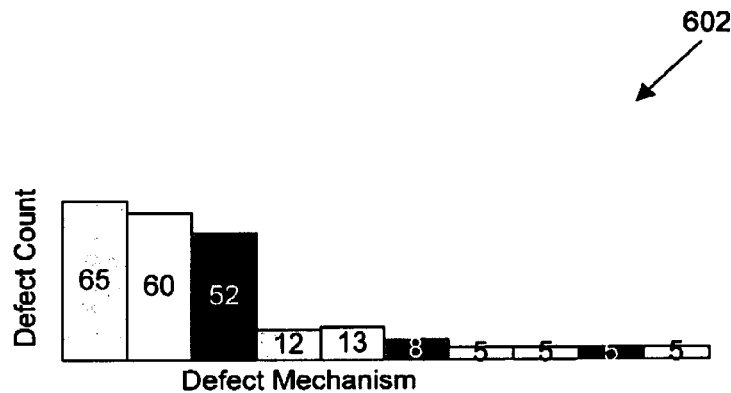
FIG. 6A illustrates a pareto chart having a plurality of bars for each defect type on a particular wafer, where the bar height represents a defect count.
Figure 6B:
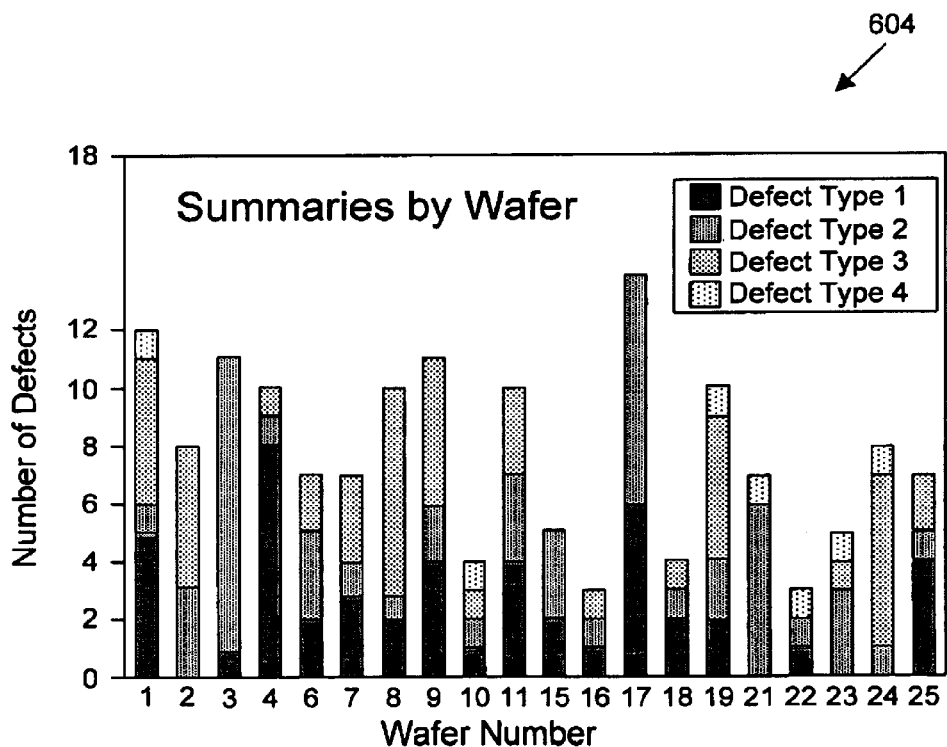
FIG. 6B illustrates a multiple wafer pareto chart having a plurality of bars for each wafer, where each bar is divided into sub-bars of different defect types.

After a recipe is loaded for the specimens or wafers loaded in the Defect Analysis System 100, the wafers are then automatically inspected for potential defects and the potential defects are analyzed in operation 210. This automatic defect analysis process generates defect information in operation 212. For example, pareto charts of the various defect types are generated and presented to the user in application interface 158. FIG. 6A illustrates a pareto chart 602 having a plurality of bars for each defect type of a wafer type specimen, where the bar height represents a defect count. FIG. 6B illustrates a multiple wafer pareto chart 604 having a plurality of bars for each wafer, where each bar is divided into sub-bars of different defect types. Each sub-bar of FIG. 6B has a height corresponding to the defect count for such defect type. This defect information is also preferably fed back into the defect analysis operation 210 for any number of purposes which will be described further below, such as adjustment of the inspection process or recipe.

Figure 3:
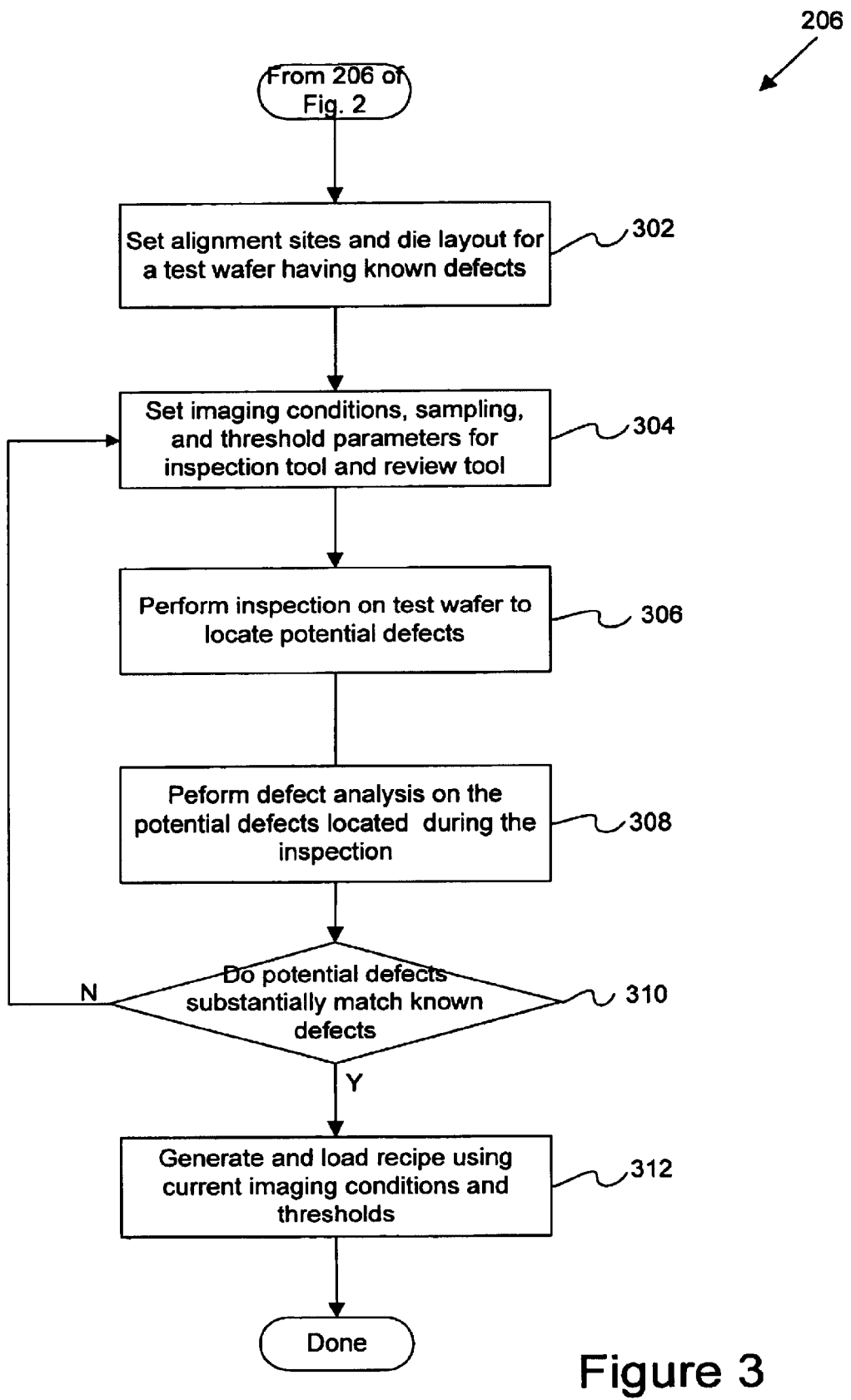
FIG. 3 is a flowchart illustrating the operation of FIG. 2 for generating and loading a new recipe in accordance with one embodiment of the present invention.

FIG. 3 is a flowchart illustrating the operation 206 of FIG. 2 for generating and loading a new recipe in accordance with one embodiment of the present invention. Initially, the alignment sites and die layout for a test wafer having known defects are set in operation 302. The alignment sites and die layout may be obtained in any suitable manner. For instance, these parameters may be automatically obtained from the reticle layout or from a database which contains such parameters. These parameters may also be manually set by an operator.

Imaging conditions and threshold parameters for the inspection tool and review tool may then be set in operation 304. The imaging conditions may include any suitable operating conditions of the inspection and review tools which are selectable by the user. In an optical type inspection or review tool, the imaging conditions may include resolution, noise suppression parameters, focus, an optics mode (e.g., darkfield or brightfield mode), a pixel size, and thresholds. In an electron beam based inspection or review tool, the imaging conditions may include landing energy, beam current density, scan pattern, spot size, acceleration voltage, wafer bias, and field of view size. The imaging conditions may also include parameters which are common to both tools, such as die size, die layout, die origin, flat or notch position, device layer, and alignment site image.

Figure 5:
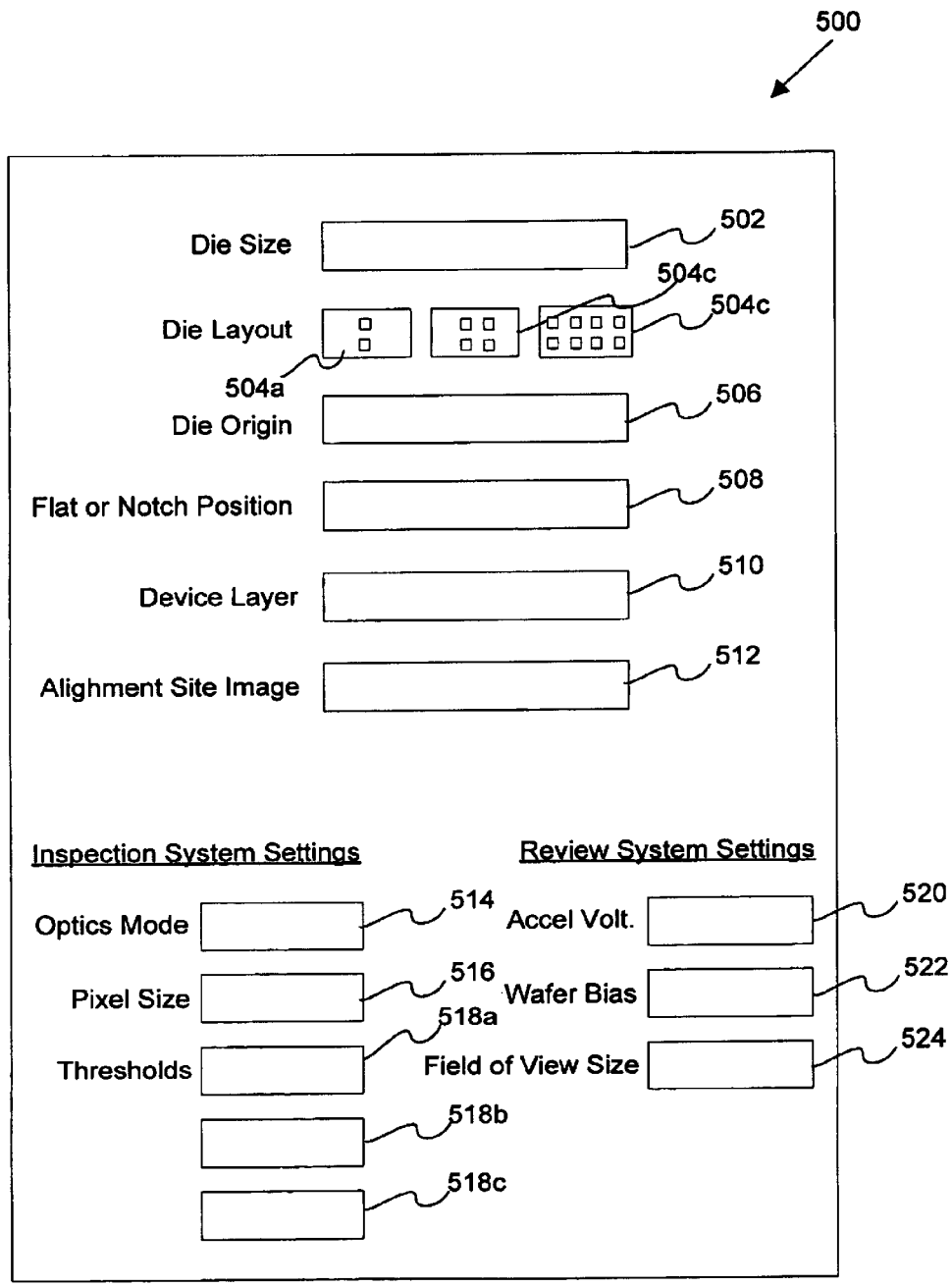
FIG. 5 is a diagrammatic illustration of an example interface for inputting recipe parameters for inspection and review in accordance with one embodiment of the present invention.

FIG. 5 is a diagrammatic illustration of an example interface 500 for inputting recipe parameters for inspection and review in accordance with one embodiment of the present invention. As shown, the interface 500 includes a number of input mechanisms for selecting parameters. These input mechanisms may take any suitable form, such as an input boxes, pull down menus, or selection buttons.

A portion of the parameters are preferably common for both the inspection and review tool. That is, the common parameters only need to be set once for both tools. In the illustrated embodiment, the common parameters include a Die Size 502, a Die Layout 504, a Die Origin 506, a Flat or Notch Position 508, a Device Layer 510, and an Alignment Site Image 512. A user may then enter a Die Size value which corresponds to the size of each die. The user may also select a particular Die Layout, such as a two-die layout 504a, a 4-die layout 504b, or an 8-die layout 504c. These die layouts are merely exemplary and are not meant to limit the scope of the invention. The Die Origin value is selected to be relative to the alignment site image. The Flat or Notch Position may indicate an orientation of the wafer's notch in terms of degrees. The Device Layer may be identified by name, e.g., poly, metal1, etc. A position value may also be entered for the Alignment Site Image.

The parameters also include settings for the inspection system, as well as the review system. In the example of FIG. 5, the inspection system settings include an optics mode (e.g., bright field or dark field mode), a Pixel Size, and one or more threshold parameters. The review system setting in this example include an Acceleration Voltage, a Wafer Bias, and a Field of View Size.

The threshold parameters are generally used by the inspection tool to determine whether a discrepancy in the test wafer represents a potential defect. The threshold parameters may include one or more predefined threshold values for particular inspection areas of the test wafer. For instance, when a particular area of a reference wafer is subtracted from a same area of the test wafer, a difference that is greater than the corresponding predefined threshold is defined as a potential defect. Different thresholds may be selected for different portions of the image. Thus, the sensitivity of the inspection tool to capturing defects is directed related to the threshold parameters.

After the imaging conditions and threshold parameters are set during this set up procedure, the recipe is then automatically optimized. An inspection is performed on the test wafer to locate potential defects in operation 306. A defect analysis is then performed on the potential defects located during the inspection in operation 308. It is then determined whether the potential defects found during inspection substantially match the known defects in operation 310. For instance, during the defect analysis, the potential defects found during the inspection are classified into defect types or nuisances. When the determined class of the defects found during inspection are substantially the same as the classes of the known defects, then it is determined that the potential defects substantially match the known defects.

If there is no match, the imaging conditions and thresholds for either the inspection tool or the review tool may then be adjusted in operation 304. In one implementation, the review imaging conditions may be automatically selected and fixed based on the particular process of the specimen, while the inspection imaging conditions and/or the threshold parameters are adjusted until a match occurs. Alternatively, the review imaging conditions may also be adjusted until a match occurs. Operations 304 through 310 are repeated until the potential defects substantially match the known defects in operation 310. After the potential defects substantially match the known defects, a recipe is generated and loaded using the current imaging conditions and thresholds in operation 312.

Figure 4A:
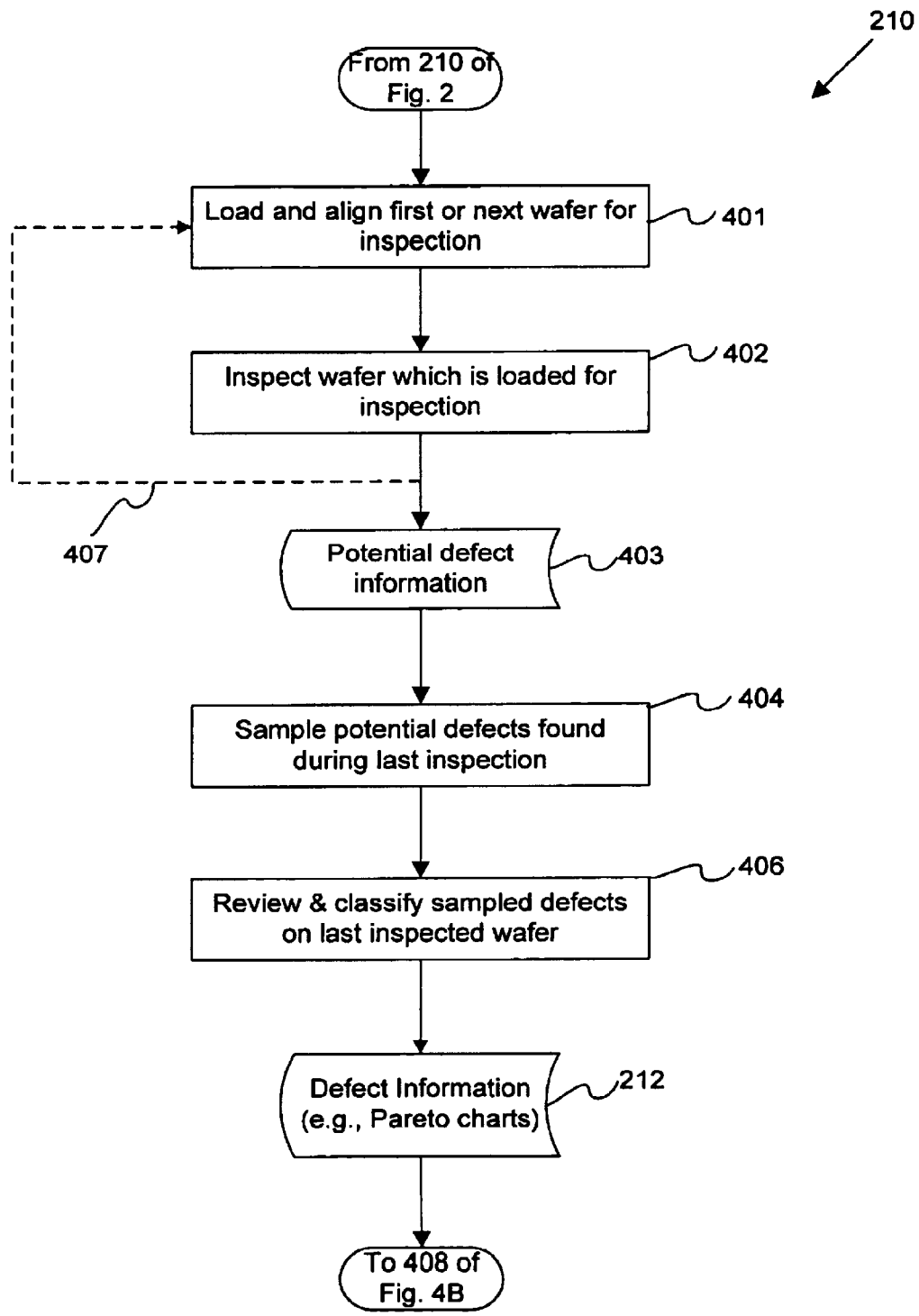
FIGS. 4A and 4B show a flowchart illustrating the operation of FIG. 2 for automatically performing inspection and defect analysis after a recipe is loaded in accordance with one embodiment of the present invention.
Figure 4B:
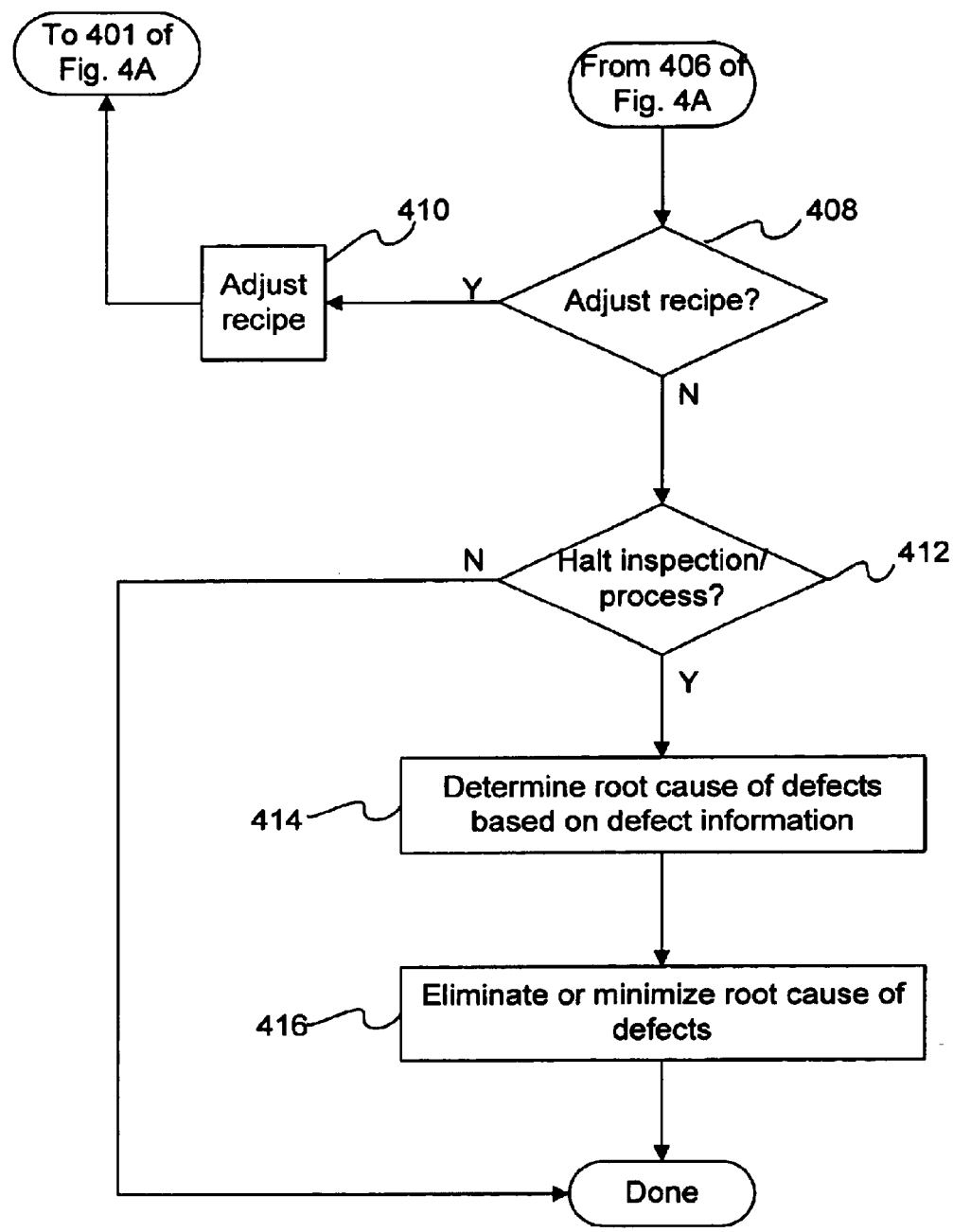

FIGS. 4A and 4B show a flowchart illustrating the operation 210 of FIG. 2 for automatically performing inspection and defect analysis after a recipe is loaded in accordance with one embodiment of the present invention. Initially, a first or next wafer is loaded and aligned for inspection in operation 401. The alignment may be based on the loaded recipe's previously selected alignment parameters.

The loaded wafer is then inspected in operation 402. The inspection results in information for a plurality of potential defects 403. In one embodiment, the potential defects information 403 is in the form of a wafer map which includes the coordinates for each potential defect. The potential defects that were found during the last inspection of the last loaded wafer are then sampled using the potential defects information (e.g., defect map) in operation 404. That is, a predefined number of the potential defects are selected for review. The predefined sampling number may have been previously set during the recipe set up procedure or may be randomly generated or a fixed value.

The sampled potential defects of the last inspected wafer may then be analyzed in operation 406. This defect analysis results in defect information 212. For instance, well known automatic defect classification procedures may be implemented for determining a plurality of defect types of the potential defects. Defect types may include a false defect type or nuisance classification, as well as "real" defect types, such as a different composition and sizes of particles, different sizes and locations of voids within a material, an electrical short or an electrical open type defect, a macro or micro scratch type defect, unremoved material, extra material, misaligned features, pattern masking defects, or any other defect types or classifications. Several embodiments for classifying defects are further described in U.S. Pat. No. 6,104,835, issued 15 Aug. 2000, by Ke Han, which patent is incorporated herein by reference in its entirety for all purposes. The review and classification 406 results in defect information 212, such as pareto charts showing the count of each defect type.

Referring to FIG. 4B, it may then be determined whether the current recipe requires adjustment in operation 408. This determination is based on the resulting defect information 212. For example, the recipe may be adjusted when the defect information indicates the defect density is too high or too low, the nuisance defect rate is too high, if a critical defect type is missing, or if a recipe is unstable run to run. If the recipe requires adjustment, the recipe is adjusted or recalibrated in operation 410 and a next wafer is loaded and aligned for inspection in operation 401.

If the recipe requires no adjustment, it may also be determined whether the inspection or current process is to be halted in operation 412. For example, the defect information may indicate that the process or imaging conditions of the inspection or review tools are beginning to drift out of specification. In this case, the drifting inspection, review, or process tool may be re-calibrated and the defect analysis process resumed.

In one implementation, if the inspection or a process is to be halted, a root cause of the defects may be determined based on the defect information in operation 414. The root cause may then be eliminated or minimized in operation 416. For example, a process, an inspection, or review parameter may be adjusted and the defect inspection and analysis process resumed. If the inspection or process is not to be halted or is resumed, a next wafer may then be loaded and aligned for inspection in operation 401.

In parallel to the defect analysis of operation, a next wafer may be loaded and aligned for inspection represented by dashed line 407 of FIG. 4A. If a problem is found during the parallel review process, the inspection may be efficiently halted prior to inspection of the entire wafer lot, for example. Additionally, the inspection procedure may be adjusted based on the defect information obtained from the review procedure. Accordingly, the Defect Analysis System of the present invention provides on the fly adjustment of inspection and/or process procedures on a wafer per wafer basis.

Although the foregoing invention has been described in some detail for purposes of clarity of understanding, it will be apparent that certain changes and modifications may be practiced within the scope of the appended claims. It should be noted that there are many alternative ways of implementing both the process and apparatus of the present invention.

For example, the specimen may be any substance or object that is suitable for inspection and review, such as a semiconductor wafer or reticle. By way of alternative examples, the present invention may be especially useful in inspecting thin film heads within hard disks, which are being designed with smaller and smaller dimensions. By way of another example, reticles may also be inspected for defects and the reticle defects reviewed. Accordingly, the present embodiments are to be considered as illustrative and not restrictive, and the invention is not to be limited to the details given herein, but may be modified within the scope and equivalents of the appended claims.

What is claimed is:

1. A method for analyzing defects on specimens, comprising:

receiving selection of a recipe for performing an inspection of the specimens for potential defects using an inspection tool and for performing a defect analysis of the potential defects using a review tool that differs from the inspection tool, wherein the recipe is received in a single interface; and automatically setting up the inspection tool based on the recipe and then inspecting the specimens for potential defects using the inspection tool to thereby locate a plurality of potential defects on the specimens; and automatically setting up the review tool based on the recipe and then analyzing the potential defects using the review tool, wherein the analysis of the potential defects results in defect information.

2. A method as recited in claim 1, wherein the defect information is in the form of defect classifications of the potential defects.

3. A method as recited in claim 2, wherein the defect information is in the form of pareto charts having a plurality of bars, wherein each bar represents a particular defect type and has a height corresponding to a number of defects found with the particular defect type.

4. A method as recited in claim 1, wherein the recipe is selected by selecting an existing recipe when an existing recipe for the specimens is available and generating a new recipe when there is no existing recipe available for the specimens.

5. A method as recited in claim 4, wherein generating a new recipe comprises:

providing a test specimen having known defects;

setting inspection imaging conditions and one or more threshold parameters for inspecting the test specimen for potential defects and setting review imaging conditions for analyzing the potential defects of the test specimen;

under the inspection imaging conditions, performing an inspection on the test specimen to locate potential defects based on the threshold parameters;

under the review imaging conditions, performing a defect analysis of the potential defects located during the inspection;

adjusting one or more of the inspection imaging conditions, review imaging conditions, and threshold parameters until the potential defects located during the inspection and analyzed during the defect analysis substantially match the known defects of the test specimen; and generating and loading a recipe based on the inspection imaging conditions, review imaging conditions, and threshold parameters when the potential defects located during the inspection and the analyzed during the defect analysis substantially match the known defects of the test specimen.

6. A method as recited in claim 5, wherein the inspection imaging conditions and the review imaging conditions are selected from a group consisting of resolution, noise suppression parameters, focus, an optics mode, a pixel size, thresholds, a landing energy, a beam current density, a scan pattern, a spot size, an acceleration voltage, a wafer bias, and a field of view size.

7. A method as recited in claim 6, wherein setting the inspection imaging conditions and the review imaging conditions include setting parameters only once which are selected from a group consisting of a die size, a die layout, a die origin, a flat or notch position, device layer, and an alignment site image.

8. A method as recited in claim 5, wherein the defect analysis includes classifying the potential defects into defect types or nuisances and the potential defects substantially match the known defects when the classified defect types of the potential defects substantially match the known defects' types.

9. A method as recited in claim 2, wherein the operation of automatically inspecting the specimens for potential defects and analyzing the potential defects comprises:

(a) loading and aligning a first one of the specimens for inspection;

(b) inspecting the first specimen for potential defects and providing potential defect information;

(c) sampling a portion of the potential defects of the first specimen; and (d) reviewing and classifying the sampled potential defects into a plurality of defect types and providing defect information based on such review and classification.

10. A method as recited in claim 9, further comprising repeating operations (a) through (d) for a next specimen immediately after inspecting the first specimen.

11. A method as recited in claim 10, further comprising adjusting the selected recipe based on the provided defect information.

12. A method as recited in claim 10, further comprising halting further processing of the first and the next specimen based on the provided defect information.

13. A method as recited in claim 10, further comprising halting the inspection of the next specimen based on the provided defect information.

14. A method as recited in claim 10, further comprising eliminating or minimizing a root cause of one or more of the defect types based on the provided defect information.

15. A method as recited in claim 10, wherein the defect types include a false defect type.

16. An apparatus for analyzing defects on specimens, comprising:

an inspection tool for inspecting a specimen for potential defects;

a review tool for analyzing a sample of the potential defects to determine a classification of such potential defects, wherein the inspection tool differs from the review tool;

a computer system configured with an application interface to allow a user to input setup conditions for the inspection tool and the review tool during a same setup phase to thereby cause the inspection tool and the review tool automatically to set up and operate based on the input setup conditions to then provide inspection and analysis of defects for one or more specimens.

17. An apparatus as recited in claim 16, wherein the inspection tool and the review tool are integrated together into a single station.

18. An apparatus as recited in claim 16, wherein the application interface has input fields for entry of a plurality of imaging conditions and at least one threshold parameter for the inspection tool and a plurality of imaging conditions for the review tool.

19. An apparatus as recited in claim 18, wherein the computer system is further operable to generate a recipe for operation of the inspection tool and review tool based on the plurality of imaging conditions and the at least one threshold parameter for the inspection tool and the plurality of imaging conditions for the review tool entered by a user.

20. An apparatus as recited in claim 19, wherein the computer system is further operable to automatically initiate execution of the inspection tool and review tool based on the generated recipe.

21. An apparatus as recited in claim 20, wherein the computer system is further operable to automatically optimize the recipe.

22. An apparatus as recited in claim 16, wherein the application interface is implemented on either the inspection tool or the review tool and the inspection tool is located at a different station then the review tool so that the inspection tool is a physically separate device than the review tool.

23. An apparatus as recited in claim 16, wherein the defect information is provided by presenting it within the application interface.

* * * * *

UNITED STATES PATENT AND TRADEMARK OFFICE
CERTIFICATE OF CORRECTION

PATENT NO. : 6,952,653 B2  
DATED : October 4, 2005  
INVENTOR(S) : Toth et al.

It is certified that error appears in the above-identified patent and that said Letters Patent is hereby corrected as shown below:

Column 12,  
Line 44, change "then the review" to -- than the review --.

Signed and Sealed this

Sixteenth Day of May, 2006

JON W. DUDAS  
*Director of the United States Patent and Trademark Office*